(12) United States Patent
Pernot et al.

(10) Patent No.: US 8,155,725 B2
(45) Date of Patent: Apr. 10, 2012

(54) METHOD FOR OPTIMISING THE FOCUSSING OF WAVES THROUGH AN ABERRATION-INDUCING ELEMENT

(75) Inventors: Mathieu Pernot, Paris (FR); Mathias Fink, Meudon (FR); Mickaël Tanter, Bagneux (FR); Gabriel Montaldo, Paris (FR); Jean-Francois Aubry, Bourg la Reine (FR); Ralph Sinkus, Paris (FR)

(73) Assignee: Super Sonic Imagine, Paris (FR)

( * ) Notice: Subject to any disclaimer, the term of this patent is extended or adjusted under 35 U.S.C. 154(b) by 881 days.

(21) Appl. No.: 12/282,625

(22) PCT Filed: Feb. 20, 2008

(86) PCT No.: PCT/FR2008/050290
§ 371 (c)(1), (2), (4) Date: Sep. 11, 2008

(87) PCT Pub. No.: WO2008/113940
PCT Pub. Date: Sep. 25, 2008

(65) Prior Publication Data
US 2009/0093724 A1 Apr. 9, 2009

(30) Foreign Application Priority Data
Feb. 21, 2007 (FR) ...................................... 07 01235

(51) Int. Cl.
*A61B 5/05* (2006.01)
(52) U.S. Cl. .................. 600/407; 600/437; 600/476
(58) Field of Classification Search .......... 600/407–410, 600/437–466, 473–480
See application file for complete search history.

(56) References Cited

U.S. PATENT DOCUMENTS

| | | | | |
|---|---|---|---|---|
| 4,938,225 A | * | 7/1990 | Fink | 600/437 |
| 5,010,885 A | * | 4/1991 | Fink et al. | 600/443 |
| 5,331,964 A | * | 7/1994 | Trahey et al. | 600/447 |
| 5,357,962 A | | 10/1994 | Green | |
| 5,423,318 A | | 6/1995 | Li | |
| 5,428,999 A | * | 7/1995 | Fink | 73/599 |
| 5,590,657 A | * | 1/1997 | Cain et al. | 600/439 |
| 5,657,760 A | * | 8/1997 | Ying et al. | 600/439 |

(Continued)

FOREIGN PATENT DOCUMENTS
EP 0 320 303 A2 6/1989
(Continued)

OTHER PUBLICATIONS

International Search Report for International Application No. PCT/FR08/050290.

*Primary Examiner* — Sanjay Cattungal
(74) *Attorney, Agent, or Firm* — Caesar, Rivise, Bernstein, Cohen & Pokotilow, Ltd.

(57) ABSTRACT

The invention concerns a method for optimizing the focusing of waves in a zone of interest of a medium, with the waves being emitted by a network of sources to the medium through an aberration-inducing element that introduces an initially indeterminate phase shift. The method according to the invention proposes to use M−1 successive modifications of the emitted wave, each giving rise to a perturbation. According to the invention, the M perturbations are measured in the zone of interest at each modification of the phase and/or amplitude distributions, and these measurements are used to deduce optimal focusing characteristics to maximize the perturbation induced in the zone of interest.

22 Claims, 2 Drawing Sheets

U.S. PATENT DOCUMENTS

| | | | |
|---|---|---|---|
| 6,042,556 A * | 3/2000 | Beach et al. | 601/3 |
| 6,161,434 A * | 12/2000 | Fink et al. | 73/587 |
| 6,198,829 B1 * | 3/2001 | Fink et al. | 381/71.12 |
| 6,312,426 B1 * | 11/2001 | Goldberg et al. | 606/33 |
| 6,485,423 B2 * | 11/2002 | Angelsen et al. | 600/458 |
| 6,490,469 B2 * | 12/2002 | Candy | 600/407 |
| 6,508,774 B1 * | 1/2003 | Acker et al. | 601/2 |
| 6,666,833 B1 * | 12/2003 | Friedman et al. | 601/2 |
| 6,675,969 B1 * | 1/2004 | Kiyohara et al. | 206/448 |
| 6,978,028 B2 * | 12/2005 | Fink et al. | 381/77 |
| 7,101,337 B2 * | 9/2006 | Aubry et al. | 600/447 |
| 7,166,075 B2 * | 1/2007 | Varghese et al. | 600/439 |
| 7,344,509 B2 * | 3/2008 | Hynynen et al. | 601/3 |
| 7,597,665 B2 * | 10/2009 | Wilk et al. | 600/459 |
| 7,729,010 B2 * | 6/2010 | George | 358/1.9 |
| 8,016,757 B2 * | 9/2011 | Kaczkowski et al. | 600/438 |
| 8,019,572 B2 * | 9/2011 | Fink et al. | 702/189 |
| 2004/0122323 A1 | 6/2004 | Vortman | |
| 2005/0277824 A1 | 12/2005 | Aubry | |
| 2010/0056908 A1 * | 3/2010 | Giller et al. | 600/426 |

FOREIGN PATENT DOCUMENTS

FR     2 843 387 A1     3/2004

* cited by examiner

METHOD FOR OPTIMISING THE FOCUSSING OF WAVES THROUGH AN ABERRATION-INDUCING ELEMENT

CROSS-REFERENCE TO RELATED APPLICATIONS

This national stage application claims the benefit under 35 U.S.C. §371 of International Application No. PCT/FR2008/050290 filed on Feb. 20, 2008, entitled METHOD FOR OPTIMISING THE FOCUSSING OF WAVES THROUGH AN ABERRATION-INDUCING ELEMENT, which in turn takes its priority from French Application No. 07 01235 filed on Feb. 21, 2007, and all of whose entire disclosures are incorporated by reference herein.

BACKGROUND OF THE INVENTION

1. Field of Invention

This present invention relates to the general area of the focussing of waves within a medium. More precisely, the invention concerns imaging procedures that require the focussing of waves through highly heterogeneous media. The applications of this type of imaging are many and varied. In particular they include under-water acoustics, telecommunications, geophysics, non-destructive testing of materials, medicine, and so on. In this last field, the focussed waves are used in imaging and in therapy for example, in particular in the case of focussed ultrasound waves.

2. Description of Related Art

The aberrations introduced by the heterogeneous media are a problem in each of these applications.

In fact, whenever a high intensity is conveyed by the waves, or whenever it is very important that only a determined zone be subjected to the waves, the aberrations are very disadvantageous, and can even prevent the use of focussed waves in certain applications due to the impossibility of achieving accurate focussing. Certain applications, in the field of the therapy for example, in fact require that the focussing be very accurate, in order not to broaden the zone of action of the focussed waves.

At present, the precision required in such applications is rendered accessible at the cost of high execution complexity, and, in the case of therapy, at the cost of invasive surgery.

In fact, in order to be able to achieve accurate focussing of high-intensity ultrasound waves in the context of brain therapy, a first solution, described in document FR 2 843 874, is to make use of the results of imaging the brain of the patient, obtained by tomographic scanning (Computed Tomography or the CT scan) performed prior to treatment. The information, in three dimensions, on the structure of the cranial bones is then used to simulate the aberrations, and to correct the signals emitted during the treatment. These digital simulations generally take quite a long time, which is incompatible with real-time working.

The patient then has to be repositioned in a magnetic resonance imaging appliance in order to allow monitoring of the real-time treatment, generally by imaging of the temperature rise.

It is then necessary for the patient to be repositioned in relation to a reference base which is identical to that used during the CT scan, in order that the structures are positioned identically. This involves a reconfiguration procedure that is generally complex. Stereotaxy frames, screwed onto the head of the patient can be used in particular.

A second solution is based on the temporal return of the waves. It consists of implanting a miniature ultrasound probe emitting ultrasound waves onto a surgical instrument that is being used during a biopsy. During the removal of tissue, the probe emits ultrasound waves in the vicinity of the tumour, and these are picked up and recorded as they exit from the cranium by a network of ultrasound transducers.

If the biopsy reveals a need for treatment, the recorded signals are then returned temporally. During their re-emission, the returned signals then focus automatically on the zone in which the biopsy was executed, that is on the tumoral zone. It is nevertheless necessary for the patient to be repositioned correctly in relation to the network of transducers and this, again, can be a difficult operation.

Then, in practice, to perform the treatment, the beam is moved electronically around the initial focal point to treat all of the tumour, point by point.

This last solution is invasive, and therefore has all of the drawbacks inherent in the invasive methods.

The use of focussed waves in the medical context, in particular the use of focussed high-intensity ultrasound waves, is therefore not favoured at present whenever elements introducing aberrations are located in the path of the waves. However ultrasound waves have some major advantages, among which are the ability to act at any time in the event of relapse or recurrence, and the ability to act on children for whom the therapeutic options are more limited than for the adult.

It should also be emphasised that the use of high-intensity ultrasound waves is an operation that is free of irradiation, and is effected by the local raising of temperature only.

All of the means that allow extension of the field of use of ultrasound waves, and more generally of the radiation-free waves, are therefore worthy of the highest interest. In particular, those means that allow the influence of aberrations to be eliminated figure amongst the means mentioned.

PURPOSE AND SUMMARY OF THE INVENTION

This present invention therefore has as its main objective to enable the achievement of correct focussing of waves, even in the presence of an aberrating element while still avoiding the drawbacks exhibited by the two existing solutions, namely the complexity of a reconfiguration between two imaging procedures, accompanied by risks of errors and, in the case of guidance by biopsy, the invasive character of the procedure.

To this end, the invention proposes a method for optimising the focussing of waves in a zone of interest of a medium, with the waves being emitted by a network of N sources to the medium through an aberration-inducing element that cause a phase shift which is initially indeterminate $\phi_n$ ($1 \leq n \leq N$), where the method uses M−1 successive modifications of the emitted wave, each giving rise to a perturbation, where the M perturbations are measured, and these measurements are used to deduce optimal focussing characteristics, and include the following steps:

a) the emission, by a network of N sources, of waves $A_n \cdot e^{j\alpha_n}$ (with j denoting a complex number, where $j^2=-1$) exhibiting a spatial phase distribution $\alpha_n$ and an amplitude distribution $A_n$ ($1 \leq n \leq N$), and propagating to the zone of interest in the medium, b) M−1 (M>1) modifications of the spatial phase distribution $\alpha_n$ and/or of the amplitude distribution $A_n$ ($1 \leq n \leq N$) of the waves emitted simultaneously by a plurality of sources in the network, with each modification corresponding to simultaneous modifications of the phases and/or amplitudes of this plurality of sources in the network, and each engendering a step a) of emission, c) measurement of at least one perturbation $I_m$ ($1 \leq m \leq M$) induced by the waves in the zone of interest at each modification m ($1 \leq m \leq M$) of the phase $\alpha_n$ and/or amplitude $A_n$ distribution, (d) deduction, from the perturbation measurements $I_m$, of an optimal emission phase distribution $\alpha_{n_{opt}}$ and/or an amplitude distribution $A_{n_{opt}}$ maximising the perturbation induced in the zone of interest.

Such a method proposes adaptation of the focussing using the measurement of at least one perturbation induced by the focussed wave in the theoretical focal zone in order to optimise the phase shifts in all the transducers generating the focussed wave, or at least in a large number of them. The perturbation is generated remotely in the zone of interest by the network of emitters.

The term "perturbation" refers to a reversible or irreversible modification of certain physical parameters of the medium resulting from the interaction between the wave and the medium associated with the energy density or of the mean power transported by the wave in the zone of interest or of an energy density in the zone of interest.

An important consequence of this restrictive definition of the perturbation is that the amplitude of the perturbation is linked only to the amplitude of the wave, or to its energy, of the wave in the zone of interest, and not to its phase at any given instant. The perturbation can, for example, be a local temperature rise resulting from the absorption of the wave by the medium, a movement, or a local deformation of the medium, resulting from the radiation force exerted by the wave, or indeed the appearance of a cavitation bubble, a energy retrodiffused by the zone of interest, a density of acoustical, ultrasonic, electromagnetic or optical energy in the zone of interest.

Measurement of the perturbation is rendered possible by the fact that the perturbations are induced into the medium by several sources in the network at the same time, and not successively by a single source. This ensures that the energy emitted into the medium is sufficient to induce a perturbation that is distinguishable by the measurement system and that the modifications, effected on a plurality of sources simultaneously, generate perturbations that can be distinguished from each other. Optimal focussing is deduced from the successive emissions effected each time, with several sources in the network, after successive modifications of the phase and/or amplitude distribution.

The term "zone of interest" refers to a zone of the tissue in which it is desired to focus the waves in order to attain a maximum of energy there spatially. Typically, by the focussing of waves, one is seeking to attain a peak of energy in a zone of interest that is limited to an extension a few hundred μm in depth and laterally in the ultrasound field. More generally, a zone of interest for a given procedure using waves has a dimension in the neighbourhood of the wavelength used.

The invention is particularly useful in the context of brain therapy, in which it is necessary to locate the zone to be necrotised, typically a tumour, very precisely, and not to go outside of this zone so as not to cause damage to healthy tissue. Treatments by high-intensity focussed ultrasound beams are therefore particularly concerned by the invention.

In this context, with the aid of the invention, correction of the focussing can be achieved just before the treatment, using a single network of transducers for the correction of focussing, for the treatment, and indeed for the imaging.

Moreover, since it allows intervention with neither trephination nor the introduction of surgical instruments, the invention offers an operating quality and a convenience which has not been available hitherto.

In particular, the invention renders easy non-invasive therapies for cerebral lesions. Since these therapies are advantageous from the viewpoints of cost and risk, then the invention therefore meets the current socioeconomic challenges in the field of near-surgical interventions.

According to an additional advantageous characteristic, the method according to the invention also includes a step c') for the measurement of at least one perturbation $I_{m_e}$ at a point located outside of the zone of interest [6] at each modification m ($1 \leq m \leq M$) of the phase $\alpha_n$ and/or amplitude $A_n$ distribution, with step d) then being a deduction step, from perturbation measurements $I_m$ and from perturbation measurements $I_{m_e}$, of an optimal emission phase distribution $\alpha_{n_{opt}}$ and/or an amplitude distribution $A_{n_{opt}}$ maximising the perturbation $I_m$ induced in the zone of interest [6] and minimising the perturbation or perturbations $I_{m_e}$ outside the zone of interest.

This additional advantageous characteristic allows even greater concentration of the energy sent into the medium to the zone of interest and not outside of the latter. This characteristic therefore allows one to control the extent of the perturbation, which is ideally limited to the zone of interest.

More generally, at each modification, several measurements of the perturbation can be effected at several points in the medium.

According to a first embodiment of the invention, the spatial phase distribution $\alpha_n$ ($1 \leq n \leq N$) is modified by successive iterations of the phases applied to at least a plurality of sources, with the optimal phase distribution $\alpha_n$ being chosen as the iteration that generates the maximum perturbation.

According to this characteristic, an empirical iteration is performed, and the choice of the optimal phase distribution to be applied to the plurality of tested sources is effected from among the phase distributions tested during the iteration. Measurement of the intensity of the perturbation induced in the focal zone at each iteration, and the choice of the phase distribution on the plurality of sources resulting in the largest perturbation allows us to choose the optimal phase distribution or amplitude distribution for the plurality of sources.

According to one advantageous characteristic, since the phase distribution $\alpha_n$ is broken down into a base of K vectors $V_k$ ($1 \leq k \leq K$) with $$\alpha_n = \sum_{k=1}^{K} d_k V_{kn}$$

where $d_k$ is a real number, with each particular vector $V_k$ describing the phases emitted by the N sources, the phase modifications $\alpha_n$ ($1 \leq n \leq N$) are effected on all the N sources by $S_k$ modifications of the value of $d_k$ for each vector $V_k$, with M then being equal to $$\sum_{k=0}^{K} S_k.$$

Such a characteristic is used to select and/or simultaneously weight all the sources in order to constitute the plurality of sources. This approach has two advantages. Firstly, the definition of vectors from the spatial variations of the aberrations is used, according to the method of the invention, to effect phase modifications that directly take account of the specificities of these variations. Secondly, by emitting with all the emitters, we avoid effecting phase modifications that would have no perceptible impact on the amplitude of the measured intensity of the perturbation. This approach therefore enables us to considerably reduce the number of modifying iterations of the method. The execution of an iteration of the number $d_k$ for each vector $V_k$ is used to determine a number $d_k$ that generates an optimal phase distribution for the vector $V_k$. The re-editing of the iteration for $d_{k+1}$ associated with the following vector $V_{k+1}$ is used to converge toward an optimal focus on all the sources in the network.

Advantageously, the modifications of the phase distribution $\alpha_n$ are effected in a subspace of K' (K'<K) vectors of the base $V_k$, with $$\alpha_n = \sum_{k=1}^{K'} d_k V_{kn},$$

and M then being equal to $$\sum_{k=0}^{K'} S_k.$$

Such a characteristic is used to select a certain number of spatial frequencies from among a set of vectors describing a reduced space of spatial frequencies. This is used to reduce the time required to optimise the phase distribution.

In one advantageous implementation, the vectors $V_k$ are determined from K periodic functions of the space, with each coefficient $V_{kn}$ being determined by the value of a function k ($1 \leq k \leq K$) relative to the position of the source n.

The periodic functions, which can be sinusoidal functions, are used to simply describe a particular space of spatial frequencies.

According to another advantageous implementation characteristic, the spatial amplitude distribution $A_n$ ($1 \leq n \leq N$) is modified by successive modifications to at least a plurality of sources, with the optimal amplitude distribution $A_{n_{opt}}$ being chosen as the iteration that generates the maximum perturbation.

This additional characteristic is used to add an optimisation of the amplitude as a function of the spatial frequencies in addition to optimisation of the phases.

The modifications to the amplitude distribution according to the additional characteristic can be effected successively, alternately or simultaneously with the modification of the phase distribution.

According to a second embodiment, the modifications to the amplitudes $A_n$ and the phases $\alpha_n$ are a combination of P vectors $H_p$ defined in the form of a matrix $H_{pn}$ ($1 \leq p \leq P$ and $1 \leq n \leq N$) with $$A_n \cdot e^{j\alpha_n} = \sum_{p=1}^{P} c_p H_{pn},$$

in which each value $c_p$ is a complex number.

With such a characteristic, each modification of the phase and/or amplitude distribution corresponds to a change to the value of the complex number $c_p$. Since this modification is then common to several sources designated by means of the vector $H_p$, this characteristic is used to generate a perturbation that is detectable.

With this characteristic, the optimal phase distribution is determined with the aid of the perturbation measurements used as determinants in the theoretical equations linking the phase and the energy of the perturbation.

The matrix can be an orthogonal matrix, such as a Hadamard matrix for example.

According to an advantageous characteristic, the M modifications of the phase and/or amplitude distributions are implemented by $R_p \geq 2$ modifications of the phase value $x_r$ during the emission of the sum $H_{p_1 n} + H_{pn} \cdot e^{j x_r}$ on each source (n) corresponding to the sum of at least two vectors $H_{p1}$ and $H_p$ ($1 \leq p \leq P$) of the base, one of which is phase-shifted by a phase $x_r$, with M then being equal to $$\sum_{p=1}^{P} R_p,$$

and the phase and/or amplitude distributions being determined by virtue of the measurements $I_m$ of the perturbations obtained for each sum of vectors emitted and by inversion of the matrix $H_{pn}$.

This characteristic, which consists of applying a phase shift to one of the two vectors, is used, with the aid of the theoretical equations, to obtain the value of the phase and amplitude shift $B_p \cdot e^{j\beta_p}$ introduced by the aberrating element between the two different emission vectors $H_{p1}$ and $H_p$, achieved by performing several measurements of the perturbations engendered by the successive emission of the sum $H_{p_1} + H_p \cdot e^{jx}$ for several values of x.

Deduction of the distribution of the phase shifts $\phi_n$ is obtained by inversion of the matrix $H_{pn}$ and using the $B_p \cdot e^{j\beta_p}$ obtained for each vector $H_p$:

$$A_n \cdot e^{j\phi_n} 1 = inv(H_{pn}) B_p e^{j\beta_p}$$

The optimal phase distribution $\alpha_{n_{opt}}$ to be emitted on each of the sources is then obtained directly by inversion of the phase:

$$e^{j\alpha_n} = e^{-j\phi_n}.$$

In an advantageous application of the invention, the focussing medium is a biological one.

According to the invention, the perturbation $I_m$ induced and measured in the medium can be chosen from among local movements, local velocities, stresses, or local temperature variations in the medium.

Depending on the nature of the waves and that of the medium, one of these types of perturbations will be privileged. For example, in the case of ultrasound waves, the method can be implemented with waves of an intensity such that it allows the generation of a force in the medium due to the ultrasound radiation force, but of an intensity such that it generates no damage in the medium, as would be contrarily the case during therapy.

According to another particular characteristic of the invention, measurement of the intensity of the perturbation $I_m$ induced is effected with the aid of an imaging procedure.

The use of an imaging procedure to monitor the intensity of the perturbation enables us to monitor, directly and reliably, the location of the focal point in relation to imaged structures of the medium. In the case of the therapy, this can also be used to see the lesions at the same time, and then, where appropriate, to monitor the therapeutic treatment effects in real time. This also eliminates the need to move the patient between an imaging phase and a treatment phase. Naturally, this characteristic also allows the direct location of the zone to be treated with no need to re-position the patient according to a reference base corresponding to a prior imaging step.

As an example, the micrometric movements induced by the ultrasound beam will be followed by magnetic resonance imaging. In this way, it is possible to render more flexible and more rapid the treatment protocols of cerebral tumours by allowing guidance and monitoring of the treatment using a single imaging procedure.

The imaging procedure can be chosen from among magnetic resonance imaging procedures, ultrasound imaging procedures, tomographic X-ray imaging procedures, or optical imaging procedures.

The magnetic resonance imaging procedure is particularly suitable for monitoring the changes in organic tissue, and is chosen in preference for medical applications in which, apart from the fact that this imaging is used to implement the invention, it successively and/or simultaneously allows monitoring of the effects of a treatment, or it allows the simultaneous imaging of the zone of interest that one wishes to examine, and with greater precision as the focussing of the waved improves.

The invention is thus implemented, in a quite original manner, to focus ultrasound waves in a medium that is also imaged by magnetic resonance imaging. These two procedures have the major advantage of being completely compatible and suitable for simultaneous use.

Advantageously, the measurement of the perturbation $I_m$ induced in the zone of interest is effected by imaging the zone of interest itself.

In a preferred implementation of the invention, the perturbation $I_m$ induced and measured in the medium is due to an ultrasound, sound or electromagnetic radiation force.

Such a perturbation can be measured not only as movement but also as heating. In particular, the type of measurement can be chosen as a function of the nature of the medium.

The invention also covers an emitting system that includes a) a network of N sources designed to emit focussed waves $A_n.e^{j\alpha_n}$ exhibiting a spatial phase $\alpha_n$ and amplitude $A_n$ ($1 \leq n \leq N$) distribution to a zone of interest in a medium, where the system employs a focus optimisation method in the medium, according to the invention, that is useful when the focussed waves are emitted through an element causing aberrations that introduce an initially indeterminate phase shift, where for this the system includes means, during the emission of focussed waves in the medium, to:

b) modify, M times, the spatial phase $\alpha_n$ and/or amplitude $A_n$ ($1 \leq n \leq N$) distribution of the waves emitted simultaneously by a plurality of sources in the network, with each modification corresponding to simultaneous modifications of the phases and/or amplitudes in this plurality of sources in the network, c) measure a perturbation $I_m$ ($1 \leq m \leq M$) induced by the waves in the zone of interest at each modification (m) of the phase $\alpha_n$ and/or amplitude $A_n$ distribution, (d) deduce, from the perturbation measurements $I_m$, an optimal emission phase distribution $\alpha_{n_{opt}}$ and/or an amplitude distribution $A_{n_{opt}}$ maximising the perturbation induced in the zone of interest.

According to an advantageous characteristic of the invention, the sources are ultrasound emitters.

According to a preferred implementation, the different steps of the method are determined by instructions from computer programs.

As a consequence, the invention also covers a computer program on a data medium, this program being suitable to be executed in a system for the emission of focussed waves, where this program includes instructions suitable to implementing the steps of the method according to the invention.

This program can use any programming language, and be in the form of source code, object code, or intermediate code between source code and object code, such as in a parallel compiled form, or in any other form desired.

The invention also covers a data medium that can be read by a system according to the invention, and that includes computer program instructions as mentioned above.

The data medium can be any entity or device capable of storing the program. For example, the support can include a means of storage, such as a ROM, such as a CD ROM or a microelectronic circuit ROM, or indeed any means for magnetic recording, such as a diskette (floppy disk) or a hard disk or a memory card for instance.

Secondly, the data medium can be a transmissible medium such as an electrical or optical signal, which can be routed via a electrical or optical cable, by radio or by any other means. The program according to the invention can in particular be downloaded over a network of the Internet type.

Alternatively, the data medium can be an integrated circuit into which the program is incorporated, with the circuit being suitable for execution or to be used in the execution of the method in question.

BRIEF DESCRIPTION OF THE DRAWINGS

Other characteristics and advantages of this present invention will emerge from the description that follows, with reference to the appended drawings that illustrate an embodiment example that includes nothing of a limiting nature. In the figures:

FIG. 2 presents a situation for optimising the focussing according to the method of the invention, FIG. 3 represent the frequency field of the meaningful spatial variations of the aberrations engendered by passage through the aberration-inducing element, FIG. 4 gives an example of correction of the aberrations engendered by passage through the aberration-inducing element, using a focus optimisation method according to the invention.

DETAILED DESCRIPTION OF ONE EMBODIMENT

Figure 1:
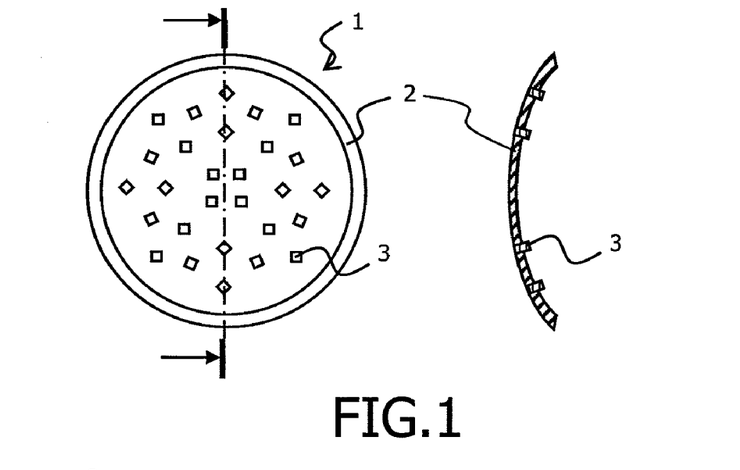
FIG. 1 describes an ultrasound probe as used advantageously to implement the invention.

FIG. 1 represents an ultrasound probe 1 as advantageously used to implement the invention. The ultrasound probe 1 presented in this figure is particularly intended to allow optimisation of the focussing of ultrasound waves in the brain.

In fact, the invention is particularly useful in this context, since the cranial bones unavoidably introduce phase aberrations within a focussed beam. These aberrations prevent accurate location of the focal zone, and this can prove to be a particular problem in medical applications in which a high degree of precision is required.

However, the cranial bones are relatively transparent to ultrasound. There is therefore an opportunity to develop solutions to correct the aberrations induced by passage through the cranial bones, in order to be able to use the ultrasound waves, despite the aberrations, to image or to treat a zone of the brain.

The ultrasound probe 1 thus includes a chassis 2 forming a portion of a sphere whose radius of curvature is chosen as a function of the application in question. In the example chosen, for imaging and treatment of the brain, the radius of curvature will be 120 mm for example. The chassis 2 includes a given number N of piezoelectric transducers 3.

In one practical embodiment, N=512 piezoelectric transducers 3 are thus installed on the chassis 2. They constitute so many wave sources. For simplicity of the representation, only a few of the transducers are represented in FIG. 1, which is merely illustrative. Each individual transducer element 3 is designed to emit an ultrasound wave, in a continuous and/or discontinuous manner. In one embodiment example, each individual element 3 has a diameter of 8 mm, and continuously emits a sine wave at the centre frequency of 1 MHz.

Conventionally, when a probe emits a beam of ultrasound waves, the phases of the waves emitted by each transducer element of the probe are calculated individually in order to achieve focussing in a zone known as the focal zone of the medium.

The phases initially calculated to perform this focussing are unable however to take account of the aberrations introduced by the heterogeneities of the medium in which the waves have to be focussed. These aberrations are unknown in fact. The invention is used to attenuate or even to eliminate the effect of these aberrations.

Figure 2:
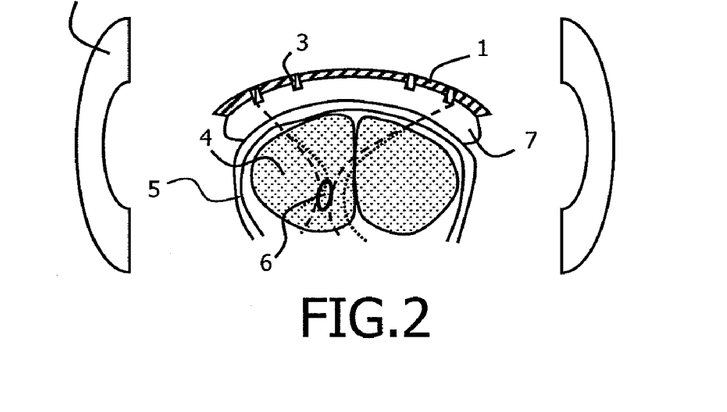

FIG. 2 represents the use of an ultrasound probe 1, as presented in FIG. 1, for imaging or therapy within a medium 4, in this case the brain, enclosed in its cranium, which is the element introducing the aberrations 6. The transmission of the waves from the transducers 3 to the cranium 5 and the brain 4 is effected by a medium 7 of suitable impedance.

The desired focussing, illustrated by dashed lines, determine a focal zone 6. In the absence of phase correction, we observe a degradation of the focussing, as represented by dotted lines in FIG. 2. This degradation is due to the presence of the aberration-inducing element 5 composed of the cranium placed in the path of the ultrasound beam emitted by the probe 1.

At the focal zone 6, the contribution (p) of the nth transducer element 3 to the total acoustic field achieved in the focal zone 6, after propagation through the cranial bone, can be written as:

$$p_n(t) = A_n D_n e^{j\alpha_n} e^{-jK_w R_c} e^{j2\pi f t} e^{j\phi_n},$$

in which $\phi_n$ is the phase shift introduced by the medium introducing aberrations 5, $A_n$ is the amplitude on emission, $\alpha_n$ represents the phase in the phase distribution corresponding to the transducer element n, $D_n$ is an attenuation factor introduced by the absorption phenomena during the passage through the cranium 5 and by the loss of amplitude by diffraction, f is the frequency of the emitted wave, $K_w$ is the wave vector and $R_c$ is the radius of curvature of the emission system.

The total acoustic field is therefore given by the equation:

$$P(t) = e^{j2\pi f t} e^{-jK_w R_c} \sum_n A_n D_n e^{j\varphi_n} e^{j\alpha_n}$$

This total acoustic field generates a perturbation I in the medium 4.

In the invention, the intensity I of the perturbation is monitored with the aid of measurements effected in the medium 4, at the focal zone 6. The measurement of the intensity I of the perturbation is advantageously effected using an imaging modality 8, such as the magnetic resonance imaging for example or echography indeed.

However, these imaging procedures do not allow direct and remote measurement of the added pressure induced by the ultrasound field. On the other hand, in the case of ultrasound waves, the local ultrasound energy can be estimated directly.

This ultrasound energy is proportional to the square of the added pressure induced by the ultrasound field. Note however that access to the local ultrasound energy does not allow direct access to the phase information and therefore to the phase shift introduced. Also, with these imaging procedures, only optimisation by measurement of amplitude is therefore possible.

In one advantageous embodiment, the local ultrasound energy is sufficient to provoke a movement within the tissue, but without causing any damage. This movement, resulting from application of the ultrasound field to the focal zone, is then measured by imaging the tissue located in the focal zone.

Such a measurement is familiar to those skilled in the art, who can also refer to the document entitled "Visco-elastic shear properties of in vivo breast lesions measured by MR elastography", Sinkus R, Tanter M, Xydeas (T), et al., MAGNETIC RESONANCE IMAGING 23 (2): 159-165 Sp. Iss. SI February 2005, to see the characteristics in the case of the magnetic resonance imaging.

In particular, when an ultrasound imaging procedure is used to measure the perturbation, all the known techniques for the measurement of movement, including Doppler measurements, signal inter-correlation techniques, measurements of phase variations in the Fourier field, etc., can be used.

When an magnetic resonance imaging procedure is used to monitor the perturbation I, the movement at the focus can be followed using magnetic resonance imaging sequences that are sensitive to movement as a function of time. These magnetic resonance imaging sequences are used to gain access to movements sampled over a very short time of between 1 and 10 milliseconds.

For example, sequences similar to those sequences that are well known in diffusion MRI can be employed. In particular, it is known that using integration over time of the movements measured during the time of application of the magnetic field gradient during a modified MRI diffusion sequence, a two-dimensional map of the movement generated by an ultrasound transducer can be created. In each voxel of this map, the movement corresponds to the integration over a short time of the movements of this voxel during application of the force.

From the movements observed, one then deduces the ultrasound radiation force induced in the focal zone. Its force density is then expressed by the formula $f = 2aIe_z/c$, in which I is the acoustic intensity, a is the ultrasound absorption coefficient of the medium, c is the speed of propagation of the sound in the tissue, and $e_z$ is the propagation direction vector.

Assuming that the wave is locally flat at the focus, the acoustic intensity in the focal zone is then given by $$I = \frac{\langle P^2 \rangle}{Z} = \frac{1}{2Z} \left| \sum_{n=1}^{N} A_n D_n e^{j\varphi_n} e^{j\alpha_n} \right|^2,$$

in which $\langle P^2 \rangle$ is the temporal mean of the acoustic energy expressed above, and Z is the acoustic impedance of the medium.

In the embodiment examples described in what follows, the acoustic energy I is chosen to be the measurement representing the perturbation.

The invention uses fluctuations in the amplitudes of the measured perturbation $I_m$, such as the acoustic intensity for example, in the focal zone 6 when the phase delays on each of the transducer elements 3 of the ultrasound probe 1 are modified m times, according to the method of the invention.

The focussed waves can also be chosen so that they provoke a temperature rise within the medium. In this case, measurement of the perturbation by temperature rise can be effected by magnetic resonance imaging in particular, using other specific sequences.

In practice, the invention proposes to modify the phase shifts on a set of transducers while also measuring the perturbations $I_m$ induced in the zone of interest, in order to determine an optimal phase distribution from the focussing viewpoint.

Advantageously, one or more additional measurements of perturbations $I_m$ induced outside the zone of interest 6 are also effected. This is particularly easy when a magnetic resonance imaging modality is used, since this imaging allows one to observe phenomena over a relatively extended zone.

Two embodiments are presented below. Both of these use the principle of an intentional and known modification of the phase distribution in order to determine the optimal phase distribution, using measurement of the perturbation engendered in the medium.

The first embodiment uses iterative modification of the phases within the phase distribution. The phase distribution is then advantageously described with the aid of spatial vectors describing the phases of the waves emitted for each n ($1 \leq n \leq N$) of the network of N sources. The phase of the element n is then expressed for example by $$\alpha_n = \sum_{k=1}^{K} d_k V_{kn}$$

in which $d_k$ is a real number.

This base is preferably chosen to correspond to the spatial frequencies most usually observed within the variations of the aberrations introduced by the aberration-inducing element.

It so happens however, that for the targeted medical applications, the phase aberrations introduced by the biological structures, vary relatively slowly in the space. This is the case in particular of the human cranium. The optimal solution for the phase shifts can therefore be sought by modifying values associated with a limited number of vectors corresponding to a limited number of spatial frequencies. The principle therefore allows us to modify the phase in several transducers, or even all of them, by modifying only the value associated with one of the vectors.

Figure 3:
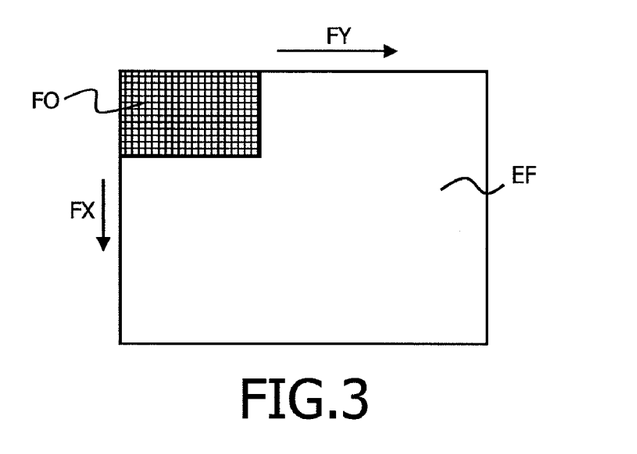

A breakdown of the spatial variations of the aberrations typically introduced by the cranium is effected, for example, by doing a Discrete Cosine Transform (DCT) on the basis of the spatial frequencies FX, FY. Such a breakdown is illustrated in FIG. 3. In this figure, it can be seen that the space of the frequencies occupied (FO) in the frequency space (EF) by the most common spatial frequencies is located in the low frequency area.

Thus, a new base of vectors, which is different from the canonical base designating each transducer one by one, is then advantageously determined by taking account of the frequency specificities of the aberrations introduced, so that each pair of non-zero spatial frequencies (FX,FY) respectively lying along the X and Y axes of the network of transducers 3 is chosen, and the corresponding spatial vector is constructed.

In one embodiment example, the vector is composed in the following manner:

$$V_k = \begin{pmatrix} \cos(P_{k_x}\pi x_1) \cdot \cos(P_{k_y}\pi y_1) \\ \cos(P_{k_x}\pi x_2) \cdot \cos(P_{k_y}\pi y_2) \\ \cos(P_{k_x}\pi x_3) \cdot \cos(P_{k_y}\pi y_3) \\ \ldots \\ \cos(P_{k_x}\pi x_N) \cdot \cos(P_{k_y}\pi y_N) \end{pmatrix}$$

where $P_{k_x}$ and $P_{k_y}$ are integers used to describe a set of spatial frequencies, $(x_n, y_n)$ is the position of the transducer n on the probe as located in a two-dimensional coordinate system and, for example, describing all the integers between 2 and 10. They can also be used to describe the same spatial frequencies FX=FY in two or other dimensions describing distinct frequencies FX and FY.

The phase distribution is then modified M times on the basis of these sinusoidal vectors, where this number can be less than the numbers (N) of transducers.

Since the phase of the source (n) can be written as $$\alpha_n = \sum_{k=1}^{K} d_k V_{kn}$$

where $d_k$ is a real number, optimising the phase distribution therefore consists of determining a set of values $d_k$, each associated with a vector $V_k$. To this end, we successively apply several values of $d_k$ to each of these vectors, for example by incrementing the value $d_k$ S times for example, in increments of 0.1 radians. At each modification, a measurement of the engendered perturbation is effected.

The number S can be identical for all of the vectors $V_k$, or can depend on the vector concerned $V_k$. It can then be denoted $S_k$.

Once the value of $d_k$ resulting in the largest perturbation has been determined for a vector, the same operation is effected for another vector by applying the optimal value to the preceding vector as the correction law, and so on.

This operation is carried out on all or part of the vectors constructed from pairs of spatial frequencies (FX,FY).

$$M = \sum_{k=1}^{K} S_k$$

modifications are thus effected. If the number of increments (S) is identical for all of the vectors $V_k$, then the total number of modifications is M=S.K.

For each modification m, at least one measurement of a perturbation $I_m$ is effected. The value $d_k$ corresponding to the modification (m) for which the maximum perturbation $I_m$ is observed is then selected.

In this embodiment, by thus optimising the phase distribution for each of these vectors $V_k$, each describing a particular pair of frequencies (FX,FY) in the space of the spatial frequencies, we optimise the focussing successively over all the spatial frequencies of the aberrations.

Then using each optimal distribution, on each vector, we get an optimal spatial distribution $\alpha_{n_{opt}}$ over all the spatial frequencies concerned.

In fact, at the end of the optimisation on each vector $V_k$, the correction for optimal phase distribution is then the sum of the vectors with which the values $d_k$ engendering the maximum perturbation are associated. By combining the optimised effect of all the vectors, the maximum perturbation is then obtained when each transducer presents the following phase:

$$\alpha_{n_{opt}} = \sum_{k=1}^{K} d_k V_{kn}$$

with $d_k$ being the optimised value. A part of the aberrations introduced by the aberrating element are then corrected. If so required, one can envisage repeating all the iterations in order to refine the optimisation.

In addition, when one or more perturbation measurements $I_{m_e}$ are effected outside the zone of interest 6, these measurements can be used to choose an optimal phase distribution which, apart from the maximisation of the perturbation $I_m$ in the zone of interest 6, allows minimisation of the perturbation $I_{m_e}$ outside the zone of interest 6. Such a minimisation can, in particular, be the subject of the second iteration used to refine the optimisation effect.

In addition, to the extent that the cranium 5 also introduces amplitude aberrations, then apart from the optimisation of the phase distribution presented above, a second-order correction using a modification of the amplitude can also be applied.

This correction is advantageously effected after a first optimisation of the phase distribution. In this case, a second optimisation of the phase distribution can advantageously be effected following on from optimisation of the amplitude.

An example of the implementation of this second-order correction consists of varying, in successive steps, generally of between 0.1 and 1, an amplitude coefficient $A'_k$ applied to each wave constructed from the phase distribution described by each vector $V_k$ in the following manner:

$$A'_k \cdot \sum_{n=1}^{N} A_n e^{j\alpha_n}$$

where $A_n$ is the default amplitude of each source.

In like manner to the phase variation, several emissions with S' different coefficients $A'_k$ are effected so as to maximise either quantity I, or the next quantity $$\frac{I}{\sum_{k=1}^{K} ACk^2},$$

in order to optimise the ratio between the intensity at the focus and the intensity emitted by the sources. For illustration, whenever S' increments are effected for all of the vectors, then an additional number of modifications are effected, of M=S'.K. in number.

Also, by successively testing several phase distributions and several amplitude factors, for each of the vectors describing the space of the spatial frequencies of the aberrations, it is possible to achieve a perturbation optimum in the focal zone and, where appropriate, a perturbation minimum outside the focal zone, revealing an optimisation of the focussing despite the phase aberrations induced by the cranium 5.

The use of vectors describing the space of the spatial frequencies of the aberrations caused by the aberrating element allows us to modify the phase on all of the transducers at the same time and, therefore, to provide the medium with sufficient energy so that the perturbation differential is measurable.

In fact, the movements of the tissue induced by the ultrasound radiation force are generally very small, of the order of 10 to 100 µm. Thus, a major limitation is the minimum movement that can be measured by the imaging procedure. This minimum movement is typically of the order of 1 µm. The energy supplied to the medium and the perturbation engendered, should therefore be sufficient to be distinguishable, given the sensitivity of the measurement.

By using phase modifications on all of the sources, the invention thus allows us to send sufficient energy into the medium not only to generate a detectable perturbation but also so that the energy differences associated with the different phase-shift combinations can be distinguished in order to allow optimisation.

The imaging procedure chosen and the device that implements it, determine the time necessary to perform a measurement corresponding to one iteration of the phase distribution. For example, with an ultrasound technology, this time is of the order of 1 ms and with the technology by magnetic resonance imaging, if we restrict ourselves to measurement in a single 3D voxel, this time is of the order of 10 ms. Thus, with the MRI technology, we get a maximum total time of 10 minutes, and the total number of iterations will be limited to 60,000.

The first embodiment described above has the advantage of using a small number of spatial frequencies, of the order of 10, in each direction X and Y and thus of allowing rapid iterative convergence to a solution that is very close to the optimal correction. About 1000 to 2000 iterations are then sufficient. With the conventional imaging procedures, this corresponds to an optimisation time of the order of 3 minutes, which is quite acceptable clinically.

The act of modifying the phase not transducer by transducer, but over the entirety of the elements or at least on a large number of them, at each step of the iteration, allows to engender modifications that are distinguishable from the acoustic intensity at the focus and thus to be less dependent on the sensitivity of measurement of the ultrasound energy in the focal zone.

Figure 4A:
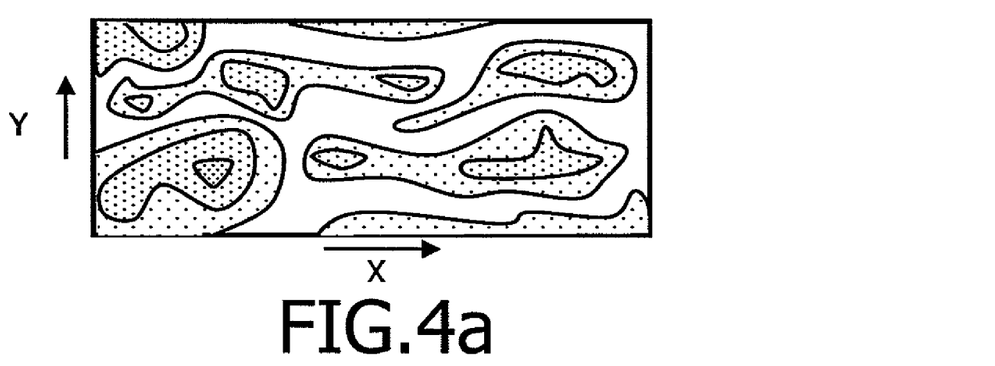
Figure 4B:
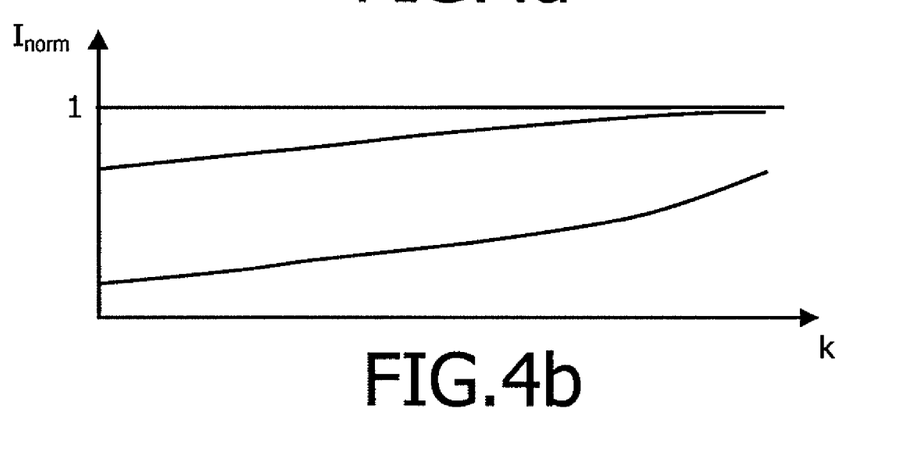

In what follows, a simulation is proposed of the method effected with a theoretical introducer of aberrations represented by a spatial distribution of phase aberrations in FIG. 4a. The process converges in about 4,000 steps, in which 10 spatial frequencies are tested in each direction (therefore K=100=10*10) and S=30 phase shifts for each eigenvector $V_k$. In FIG. 4b, the amplitude $I_{norm}$ of the acoustic energy normalised in relation to the optimal energy that would be obtained with a perfect correction is reported as a function of the number k designating each vector.

Here, optimisation is performed twice in succession for all the spatial vectors. Here, we therefore perform M=S.K modifications. It can be seen that the amplitude $I_{norm}$ of the acoustic energy at the focus increases significantly during the process. The method according to the invention thus allows convergence to a perfect focus.

Figure 4C:
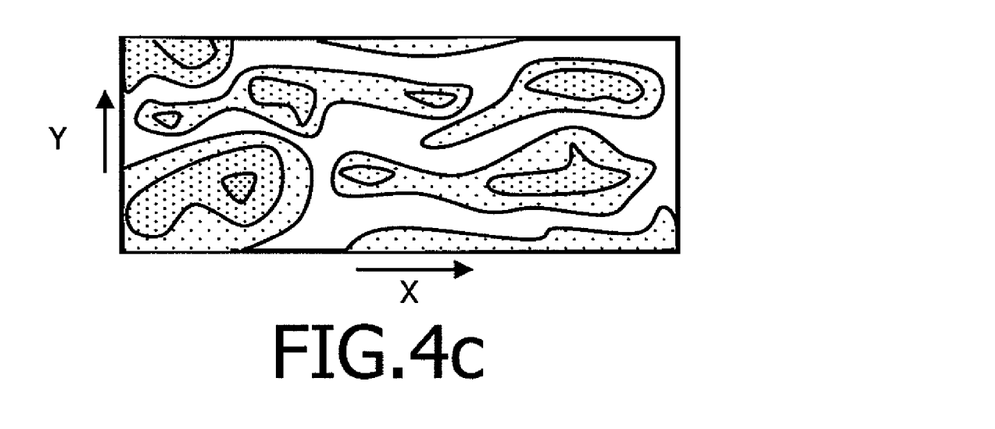

The correction law finally achieved is presented in FIG. 4c. It is very close to the theoretical aberration law introduced for the simulation and presented in FIG. 4a.

According to the first embodiment, the invention is an experimental method according to which we optimise an acoustic energy generated in a medium in order to find a phase distribution that will allow us to reduce the influence of the aberrations on focussing of the waves.

In a second embodiment of the invention, a direct inversion from the perturbation measurements is used to determine an optimal phase distribution.

It is in fact theoretically possible to estimate the optimal phase shift between two transducers from a plurality of measurements of the intensity of a perturbation generated by the interference of the waves emitted by these two transducers. In fact, the intensity generated by superimposition of the two beams in amplitude modulated by the cosine of the relative phase difference between the two transducers.

Thus, when two monochromatic beams $s_1(t)=ae^{i(\overline{\omega}t)}$ and $s_2(t)=be^{i(\overline{\omega}t+\phi)}$ interfere at a point, the intensity generated is:

$$I=a^2+b^2+2ab\cos\phi=A+B\cos\phi$$

It is therefore possible to determine the phase $\phi$ by modulation intensity. If we add an additional phase shift x to signal $s_2$, we get an intensity modulated by a cosine as a function of x:

$$I(x)=A+B\cos(\phi+x)$$

From at least three measurements of I(x), modifying x at each measurement, it is therefore theoretically possible to calculate A, B and $\phi$.

The phase of the emitted wave on each transducer is therefore modified at least twice in x distinct increments.

One way of calculating this phase shift is to effect R (R>1) measurements of the intensity for R phase modifications $x_r$, and then directly invert the system of linear equations to three unknowns, namely A, B cos($\phi$), and B sin($\phi$):

$$I(x_r)=A+B\cdot\cos(\phi)\cos(x_r)-B\cdot\sin(\phi)\sin(x_r)$$

In particular, if, for each measurement of $I(x_r)$ we also effect a measurement of $I(x_r+\pi)$ then:

$$\sum_r \cos(x_r) = \sum_r \sin(x_r) = 0$$

We can then measure two sums:

$$\begin{cases} sc = \sum_r I_r \cos(x_r) = \\ \sum [A\cos(x_r)+B\cos(\varphi)\cos^2(x_r)-B\sin(\varphi)\sin(x_r)\cos(x_r)] \\ ss = \sum_r I_r \sin(x_r) = \\ \sum [A\sin(x_r)+B\cos(\varphi)\cos(x_r)\sin(x_r)-B\sin(\varphi)\sin^2(x_r)] \end{cases}$$

$$\begin{cases} sc = B\cos(\varphi)\sum\cos^2(x_r)-B\sin(\varphi)\sum\sin(x_r)\cos(x_r) \\ ss = B\cos(\varphi)\sum\sin(x_r)\cos(x_r)-B\sin(\varphi)\sum\sin^2(x_r) \end{cases}$$

This linear system of two equations includes two unknowns, namely B cos($\phi$) and B sin($\phi$). By simply solving this system we obtain the information on the phase $\phi$ that is the phase shift introduced by the aberration-inducing element between the two transducers.

The base of the N real transducers is the canonical base. The objective of the invention is to estimate the phase shifts and amplitudes of the transducers in this canonical base:

$$T_n=A_n e^{j\alpha_n}$$

However, due to the low amplitude of each of the transducers, it is difficult to measure the modulation intensity generated by two transducers. The invention therefore consists of effecting a change of base the will allow a plurality of transducers to work together simultaneously. Many bases are possible, one being the Hadamard base:

$$H_{pn} = \begin{bmatrix} 1 & 1 & 1 & 1 & 1 & 1 & 1 & 1 \\ 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{bmatrix}$$

Let $H=H_{pn}^{(avec\ 1\leq p\leq P\ et\ 1\leq n\leq N)}$ be the change-of-base matrix. The amplitude and the phase emitted by each vector $H_p$ of this base can therefore be expressed as a complex vector describing the amplitudes and phase emitted by each vector $H_p$:

and so $H_p=H_{pn}T_n=B_p e^{j\beta_p}$ where $B_p$ and $\beta_p$ are the values of the amplitude and of the phase applied to each group of transducers of the vector designated by the vector $H_p$.

And therefore $H_p=B_p e^{j\beta_p}=H_{pn}A_n e^{j\alpha_n}$

If we take a base vector $H_{p_1}$ as the reference (phase=0 and amplitude=1), then for each vector $H_p$ ($1\leq p\leq P$), $\beta_p$ is the shift introduced by the aberrating element on vector $H_p$ in relation to vector $H_{p_1}$.

In this case, $B_p e^{j\beta_p}$ can then be estimated for each of the vectors $H_p$ by the intensity modulation method by emitting successively, for R values of $x_r$, the vector sum ($H_{p_1}+H_p\cdot e^{jx_r}$) over the network of N sources, and by measuring the perturbations induced $I_m(x_r)$ for at least two (therefore $R\geq 2$) and preferably three (R=3) distinct values of $x_r$. The amplitude and the phase as actually observed in the medium are then obtained in relation to the reference vector $H_{p_1}$ for each vector $H_p$.

This estimation of $B_p e^{j\beta_p}$ is then effected for each of the P vectors $H_p$ by carrying out R modifications of $x_r$ for each. Here we have considered that R is similar for all of the vectors.

Nevertheless, this number of modifications (R) can be a function of the vector $H_p$ and therefore denoted $R_p$. In all, $$M = \sum_{p=1}^{P} R_p$$

modifications of the phase and/or amplitude distribution are therefore effected. When $R_p=R$ is the same for all of the vectors $H_p$, then M=P.R.

Then, to obtain the phases and amplitudes introduced by the aberrator individually on each of the N sources, it is necessary to return to the canonical base. For this, it suffices to invert the matrix H. In the event that the matrix cannot be inverted, then just use the pseudo-inverted matrix obtained by breakdown into singular values, we then get the amplitude and the phase introduced by the aberrator on each of the transducers of the canonical base:

$$A_n e^{j\Phi n}=inv(H_{pn})B_p e^{j\beta_p}$$

The optimum phase of emission $\alpha_{n_{opt}}$ for each of the N sources is then obtained by inverting the phase shift:

$$e^{j\alpha_{n_{opt}}} = e^{-j\varphi_n}$$

Here it is also possible to use perturbation measurements $I_{m_e}$ effected outside the zone of interest 6. In this case, we will seek to minimise such a perturbation $I_{m_e}$.

After inversion of the matrix using the perturbations $I_{m_e}$, one obtains the aberrations introduced by the aberrating element and one can use these so as to apply a phase distribution that is both optimal for the intensity of the perturbation $I_m$ in the zone of interest 6 and the minimisation of the perturbation $I_{m_e}$ on the outside of the zone of interest 6.

Advantageously, the base H is chosen so that the measurement noise is amplified only slightly by the inversion of the matrix $H_{pn}$. This comes down, for example, to choosing a matrix H for which the eigenvectors with the greatest weight are the eigenvectors corresponding to the emission of a high intensity on the network of sources.

It can be seen finally that a variety of embodiments are possible using the principles of the invention. In particular, miscellaneous vectorial bases describing the particular spatial frequencies observed for the aberrations of the aberration-inducing element can be used.

What is claimed is:

1. A method for optimising the focussing of waves in a region of interest of a in a patient, with the waves being emitted by a network of N sources to the region through an aberration-inducing element that introduces an initially indeterminate phase shift $\phi_n$ ($1 \leq n \leq N$), with the method using M−1 successive modifications of the emitted wave, each giving rise to a perturbation, the M perturbations are measured, and these measurements are used to deduce optimal focussing characteristics, including the following steps:
   a) emission, via the network of N sources, of waves $A_n \cdot e^{j\alpha_n}$ (where $j^2=-1$) presenting a spatial phase $\alpha_n$ and amplitude $A_n$ distribution ($1 \leq n \leq N$), and propagating to the region of interest in the patient,
   b) M−1 (M>1) modifications of the spatial phase $\alpha_n$ and/or of amplitude distribution $A_n$ ($1 \leq n \leq N$) of the waves emitted simultaneously by a plurality of sources of the network, with each modification corresponding to simultaneous modifications of the phases and/or amplitudes on this plurality of sources of the network and each modification engendering a step a) of emission,
   c) measurement of at least one perturbation $I_m$ ($1 \leq m \leq M$) induced by the waves in the region of interest at each modification m ($1 \leq m \leq M$) of the phase $\alpha_n$ and/or amplitudes distribution $A_n$,
   d) deduction, from the perturbation measurements $I_m$, of a optimal emission phase distribution $\alpha_{n_{opt}}$ and/or an amplitude distribution $A_{n_{opt}}$ maximising the perturbation $I_m$ induced in the region of interest.

2. The method according to claim 1, wherein it includes a step c') for measurement of at least one perturbation $I_{m_e}$ at a point located outside the region of interest at each modification m ($1 \leq m \leq M$) of the phase $\alpha_n$ and/or amplitude $A_n$ distribution, with the step d) then being a deduction step, from the perturbation measurements $I_m$ and perturbation measurements $I_{m_e}$, of an optimal emission phase distribution $\alpha_{n_{opt}}$ and/or an amplitude distribution $A_{n_{opt}}$ maximising the perturbation $I_m$ induced in the region of interest and minimising the perturbation or perturbations $I_{m_e}$ outside the region of interest.

3. A method for the optimisation of focussing according to claim 1, wherein emitted waves are acoustical, ultrasonic, electromagnetic or optical waves.

4. The method for the optimisation of focussing according to claim 1, wherein the perturbation $I_m$ induced and measured in the region is chosen from among local movements, local velocities, stresses, temperature variations induced locally in the region, light intensity.

5. The method for the optimisation of focussing according to claim 1, wherein the perturbation $I_m$ induced and measured in the region is due to an ultrasound, sound, or electromagnetic radiation force.

6. The method for the optimisation of focussing according to claim 1, wherein the measurement of the perturbation $I_m$ induced is effected with the aid of an imaging modality.

7. The method for the optimisation of focussing according to claim 6, wherein the imaging modality is chosen from among magnetic resonance imaging modalities, ultrasound imaging modalities, and tomographic X-ray imaging modalities and optical imaging modalities.

8. The method for the optimisation of focussing according to claim 6, wherein measurement of the perturbation $I_m$ induced in the region of interest is effected by imaging of the region of interest itself.

9. The method according to claim 1, wherein the spatial phase distribution $\alpha_n$ ($1 \leq n \leq N$) is modified by successive iterations of the phases applied to at least a plurality of sources, with the optimal phase distribution $\alpha_{n_{opt}}$ being chosen as the iteration that generates the maximum perturbation.

10. The method according to claim 9, characterised in that, with the phase distribution $\alpha_n$ being broken down into a base of K vectors $V_k$ ($1 \leq k \leq K$) with $$\alpha_n = \sum_{k=1}^{K} d_k V_{kn}$$

in which $d_k$ is a real number, and with each particular vector $V_k$ describing the phases emitted by the N sources, the phase modifications $\alpha_n$ ($1 \leq n \leq N$) are effected on all of the N sources by $S_k$ modifications of the value of $d_k$ for each vector $V_k$, with M then being equal to $$\sum_{k=0}^{K} S_k.$$

11. The method according to claim 10, wherein the modifications of the phase distribution $\alpha_n$ are effected in a subspace of K' (K'<K) vectors of the base $V_k$ with $$\alpha_n = \sum_{k=1}^{K'} d_k V_{kn},$$

M then being equal to $$\sum_{k=0}^{K'} S_k.$$

12. The method according to claim 10, wherein the vectors $V_k$ are defined from K periodic functions of the space, with each coefficient $V_{kn}$ being determined by the value of a function k ($1 \leq k \leq K$) relating to the position of the source n.

13. The method according to claim 9, wherein the spatial amplitude distribution $A_n$ ($1 \leq n \leq N$) is modified by successive modifications to at least a plurality of sources, with the optimal amplitude distribution $A_{n_{opt}}$ being chosen as the iteration that generates the maximum perturbation.

14. The method according to claim 13, wherein the modifications of the amplitude distribution are effected successively, alternatively or simultaneously with the modification of the phase distribution.

15. The method according to claim 1, wherein the modifications of the amplitudes $A_n$ and of the phases $\alpha_n$ are a combination of P vectors $H_p$ defined in matrix form $H_{pn}$ ($1 \leq p \leq P$ and $1 \leq n \leq N$) with $$A_n \cdot e^{j\alpha_n} = \sum_{p=1}^{P} c_p H_{pn},$$

in which each value is a complex number.

16. The method according to claim 15, wherein the matrix $H_{pn}$ is orthogonal.

17. The method according to claim 16, wherein the matrix $H_{pn}$ is a Hadamard matrix.

18. The method according to claim 15, wherein the M modifications of the phase and/or amplitude distribution are implemented by $R_p \geq 2$ modifications of the phase value during the emission of the sum $H_{p_1 n} + H_{pn} \cdot e^{jx_r}$ on each source (n) corresponding to the sum of at least two vectors $H_{p1}$ and $H_p$ ($1 \leq p \leq P$) of the base, one of which is phase-shifted by a phase $x_r$, with M then being equal to $$\sum_{p=1}^{P} R_p,$$

the optimal phase distributions and amplitudes being determined by virtue of the measurement of the perturbations $I_m$ obtained for each sum of vectors emitted and by inversion of the matrix $H_{pn}$.

19. A computer program product stored on a non-transitory computer readable medium that includes instructions for the execution of the steps of the optimisation method according to claim 1 when the said program is executed by a computer.

20. A non-transitory recording medium that can be read by a computer, on which is recorded a computer program that includes instructions for executing the steps of the optimisation method according to claim 1.

21. An emitter system including a network of N sources designed to emit focussed waves $A_n \cdot e^{j\alpha_n}$ presenting a spatial phase $\alpha_n$ and amplitude distribution $A_n$ ($1 \leq n \leq N$) to a region of interest in a patient, with the system using a method for optimising focussing in the region according to claim 1, which is useful when the focussed waves are emitted through an aberration-inducing element introducing an initially indeterminate phase shift, and with the system including for this, during the emission of focussed waves in the region, the means to do the following:

b) to modify, M−1 times, the spatial phase distribution $\alpha_n$ and/or of amplitude distribution $A_n$ ($1 \leq n \leq N$) of the waves emitted simultaneously by a plurality of sources in the network, with each modification corresponding to simultaneous modifications of the phases and/or amplitudes on this plurality of sources of the network and engendering an emission of focussed waves in the region, c) to measure a perturbation $I_m$ ($1 \leq m \leq M$) induced by the waves in the region of interest [6] at each modification (m) of the phase $\alpha_n$ and/or amplitude $A_n$ distribution, d) to deduce, from the perturbation measurements $I_m$ ($1 \leq m \leq M$), an optimal emission phase distribution $\alpha_{n_{opt}}$ and/or amplitude distribution $A_{n_{opt}}$ maximising the perturbation induced in the region of interest.

22. A system according to claim 21, wherein the sources are ultrasound emitters.

* * * * *